(12) United States Patent
Jeong et al.

(10) Patent No.: US 7,837,943 B2
(45) Date of Patent: Nov. 23, 2010

(54) DEVICE AND METHOD FOR PRE-TREATING AND INJECTING LIQUID SPECIMEN

(75) Inventors: Sung-young Jeong, Yongin-si (KR); Hun-joo Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 1169 days.

(21) Appl. No.: 11/484,068

(22) Filed: Jul. 11, 2006

(65) Prior Publication Data
US 2007/0163366 A1 Jul. 19, 2007

(30) Foreign Application Priority Data
Jan. 19, 2006 (KR) .................. 10-2006-0005845

(51) Int. Cl.
*A61M 5/19* (2006.01)
*A61M 5/315* (2006.01)

(52) U.S. Cl. .................. 422/100; 73/1.74; 73/441; 422/99; 422/101; 604/89; 604/191; 604/220

(58) Field of Classification Search ........... 422/99–101; 73/1.74, 441; 604/89, 191, 220
See application file for complete search history.

(56) References Cited

U.S. PATENT DOCUMENTS

| | | | |
|---|---|---|---|
| 4,632,672 A * | 12/1986 | Kvitrud | 604/222 |
| 5,195,526 A * | 3/1993 | Michelson | 600/431 |
| 5,388,730 A * | 2/1995 | Abbott et al. | 222/153.13 |
| 5,785,682 A * | 7/1998 | Grabenkort | 604/82 |
| 6,409,971 B1 | 6/2002 | Wilkinson et al. | 422/103 |
| 6,921,395 B2 | 7/2005 | Carano et al. | 604/411 |
| 2003/0085024 A1* | 5/2003 | Santiago et al. | 165/104.11 |

* cited by examiner

*Primary Examiner*—Jill Warden
*Assistant Examiner*—Paul S Hyun
(74) *Attorney, Agent, or Firm*—Cantor Colburn LLP

(57) ABSTRACT

A device for pre-treating and injecting a liquid specimen includes a first syringe including an open top first tube including a first hole in the bottom and protrusions, a second syringe including an open top second tube including a second hole in the bottom and an inner diameter greater than an outer diameter of the first tube, a second piston movable along an inner wall of the second tube and including a third hole and a communication channel providing fluid communication between the first hole and the third hole, and a joint portion attachable to and detachable from a top of the second tube and including an opening corresponding to a transverse cross-section of the first tube and grooves corresponding to the shape of the protrusions such that the first tube passes through the joint portion when the protrusions are matched with the grooves.

20 Claims, 15 Drawing Sheets

DEVICE AND METHOD FOR PRE-TREATING AND INJECTING LIQUID SPECIMEN

CROSS-REFERENCE TO RELATED PATENT APPLICATION

This application claims the benefit of Korean Patent Application No. 10-2006-0005845, filed on Jan. 19, 2006, in the Korean Intellectual Property Office, the disclosure of which is incorporated herein in its entirety by reference.

BACKGROUND OF THE INVENTION

1. Field of the Invention

The present invention relates to a device for pre-treating and injecting a liquid specimen and a method of pre-treating and injecting a liquid specimen using the device.

2. Description of the Related Art

In general, biological analytic processes, such as detection of pathogenic bacteria or molecular diagnostics, include separation of target cells from samples, concentration of cells, separation of biomolecules, amplification of biomolecules, hybridization reactions and detections, etc.

Vigorous research on a lab-on-a-chips (LOC) on which a series of the biological analytical processes can be rapidly and automatically performed has been conducted. The LOC includes a microfluidic device to perform the biological analytic processes.

The microfluidic device refers to a device in which an inlet, an outlet, and a reaction chamber, etc. are in fluid communications via microchannels. The microfluidic device generally includes a micropump for transporting a fluid, a micromixer for mixing the fluid, and a microfilter for filtering the transported fluid, etc. in addition to the microchannels.

In general, the chamber of the microfluidic device contained in the LOC comprises at least one of a cell counting chamber, a cell sorting chamber, a DNA extraction chamber, a PCR amplification chamber, and a detection chamber.

A series of biological analytic processes using the LOC necessarily include collecting and pre-treating a biological sample and injecting the sample into the LOC.

For example, as a conventional device to perform the above processes, U.S. Pat. No. 6,921,395 describes a container assembly for collecting, transporting and dispensing a liquid specimen.

U.S. Pat. No. 6,409,971 describes a urine collection system device. The device is an open collection system designed to collect and transfer a liquid urine specimen into a non-evacuated tube through a valve.

However, conventional devices cannot perform all the processes of the collection, pre-treatment, and injection of the biological sample. That is, an integrated device for performing all the above processes has not been reported. Thus, there is a need for a separate injection implement or device to inject the sample into an analytical device such as the LOC after the collection and pre-treatment of the sample.

Further, the conventional devices cannot fully remove bubbles and wastes from a biological sample, for example, saliva or urine. When the sample from which the bubbles and wastes are not fully removed is injected to an analytical device, such as the LOC, clogging occurs in the microchannels, which can induce errors during the analytical processes.

SUMMARY OF THE INVENTION

The present invention provides a device for pre-treating and injecting a liquid specimen, which permits collection, pre-treatment, and injection of the specimen in an integrated manner and can fully remove bubbles and wastes from the specimen to prevent clogging in microchannels.

The present invention also provides a method of pre-treating and injecting a liquid specimen, which permits collection, pre-treatment, and injection of the specimen in an integrated manner and can fully remove bubbles and wastes from the specimen to prevent clogging in microchannels.

According to an aspect of the present invention, there is provided a device comprising: a first syringe comprising: a first tube having an open top and a first hole in the bottom; and protrusions formed in a lower and outer wall of the first tube; a second syringe comprising: a second tube having an open top and a second hole in the bottom and having an inner diameter greater than an outer diameter of the first tube; a second piston capable of moving along an inner wall of the second tube and having a third hole; and a communication channel providing a fluid communication between the first hole of the first tube and the third hole of the second piston and fixing the second piston to the first tube; and a joint portion being attachable to and detachable from a top of the second tube and having an opening having a shape which corresponds to a transverse cross-section of the first tube and grooves having a shape which corresponds to the shape of the protrusions such that the first tube can pass through the joint portion when the protrusions are matched with the grooves.

In an embodiment of the present invention, the first syringe may further comprise a first piston capable of moving along an inner wall of the first tube; and a first piston rod connected to the first piston in an upper direction of the first tube.

In an embodiment of the present invention, the second syringe may further comprise an outlet connected to the second hole of the second tube.

In an embodiment of the present invention, the second syringe may further comprise a cap being attachable to and detachable from the outlet.

In an embodiment of the present invention, the second piston may further comprise vent holes for discharging a gas.

In an embodiment of the present invention, the second piston may further comprise vent holes for discharging a gas.

In an embodiment of the present invention, the second syringe may further comprise a gas permeable membrane which is impermeable to liquid, the gas permeable membrane being connected to a bottom surface of the second piston.

In an embodiment of the present invention, the second tube may further comprise a filter membrane which is permeable to liquid but impermeable to gas, in its inner and lower portion.

In an embodiment of the present invention, the second tube may further comprise a filter membrane support supporting the filter membrane and having the form of nets.

According to another aspect of the present invention, there is provided a method of pre-treating and injecting a liquid specimen, comprising: introducing the liquid specimen into a second tube of the device according to an embodiment of the present invention; introducing a treatment solution into a first tube of the device; flowing the treatment solution in the first tube into the second tube through a communication channel by moving the first piston downwards without matching protrusions of the first syringe with grooves of a joint portion; and moving the first tube downwards with matching the protrusions of the first syringe with the grooves of the joint portion, to inject the mixed solution to an exterior device through an outlet of the second tube.

In an embodiment of the present invention, the method may further comprise mixing the liquid specimen with the treatment solution, after introducing the treatment solution.

In an embodiment of the present invention, a cap may be connected to the outlet before the liquid specimen is introduced into the second tube and the cap may be separated from the outlet before the mixed solution is injected to the exterior device.

In an embodiment of the present invention, the liquid specimen may be selected from the group consisting of saliva, urine, blood, serum, and a cell culture.

In an embodiment of the present invention, the exterior device may be a microfluidic device for performing a series of biological analytic processes.

In an embodiment of the present invention, the exterior device may be a cell lysis device.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

In an embodiment of the present invention, there is provided a device for pre-treating and injecting a liquid specimen, which permits collection, pre-treatment, and injection of the specimen in an integrated manner and can fully remove bubbles and wastes from the specimen to prevent clogging in microchannels.

Figure 1:
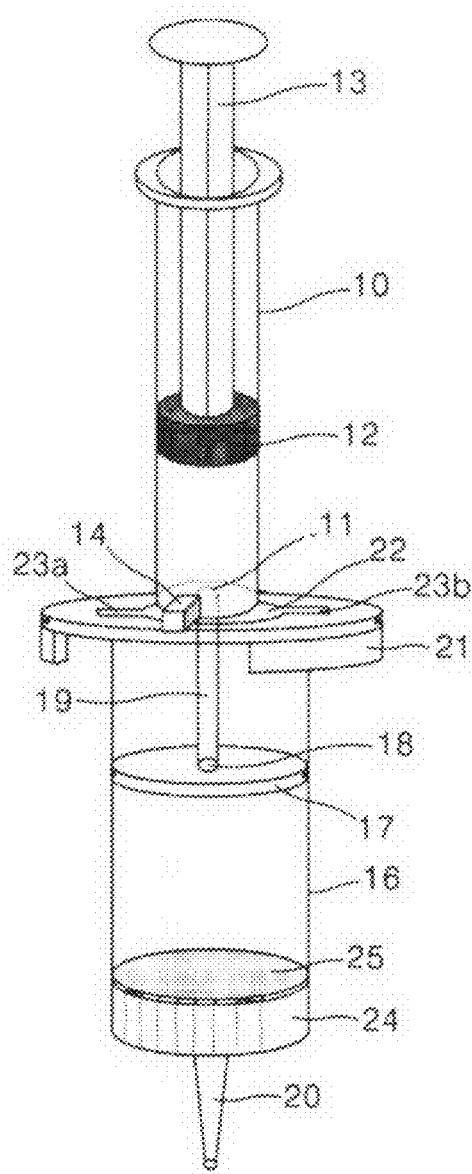
FIG. 1 is a schematic perspective view of a device for pre-treating and injecting a liquid specimen according to an embodiment of the present invention.

FIG. 1 is a schematic perspective view of a device for pre-treating and injecting a liquid specimen according to an embodiment of the present invention.

Referring to FIG. 1, the device according to an embodiment of the present invention includes a first syringe, a second syringe, and a joint portion 21.

The first syringe of the device comprises a first tube 10 having an open top and a first hole 11 in the bottom; and protrusions 14 formed in a lower and outer wall of the first tube 10.

The first syringe may further comprise a first piston 12 capable of moving along an inner wall of the first tube 10; and a first piston rod 13 connected to the first piston 12 in an upper direction of the first tube 10.

The second syringe of the device comprises a second tube 16 having an open top and a second hole (not shown) in the bottom and having an inner diameter greater than an outer diameter of the first tube 10; a second piston 17 capable of moving along an inner wall of the second tube 16 and having a third hole 18; and a communication channel 19 providing a fluid communication between the first hole 11 of the first tube 10 and the third hole 18 of the second piston 17 and fixing the second piston 17 to the first tube 10.

The second syringe may further comprise an outlet 20 connected to the second hole (not shown) of the second tube 16.

The second syringe may further comprise a cap (not shown) being attachable to and detachable from the outlet 20.

The second tube 16 may further comprise a filter membrane 25 which is permeable to liquid but impermeable to gas, in its inner and lower portion. Cells may pass through the filter membrane 25.

The second tube 16 may further comprise a filter membrane support 24 supporting the filter membrane 25 and having the form of nets.

The device for pre-treating and injecting a liquid specimen according to the present embodiment may remove bubbles and wastes etc. which may occur clogging in microchannels of a biological analytic device, such as a lab-on-a-chips (LOC), using the filter membrane 25, and thus, exclude an error which can occur during the analytic process.

The joint portion 21 of the device is attachable to and detachable from a top of the second tube 16 and has an opening 22 having a shape which corresponds to a transverse cross-section of the first tube 10 and grooves 23a and 23b having a shape which corresponds to the shape of the protrusions 14 such that the first tube 10 can pass through the joint portion 21 when the protrusions 14 are matched with the grooves 23a and 23b. Only one of two protrusions 14 is shown in FIG. 1.

Using the protrusions 14 and the grooves 23a and 23b without matching them with each other, the device has an advantage that when a treatment solution is injected into the second syringe, the first syringe is fixed on the joint portion 21 and thus, the liquid specimen is not pushed out.

Bubbles and wastes etc. which may occur clogging in microchannels of a biological analytic device, such as an LOC may be removed using the filter membrane 25, and thus, an error which can occur during the analytic process can be excluded.

Using the device for pre-treating and injecting a liquid specimen according to an embodiment of the present invention, the collection, pre-treatment, and injection of the specimen may be rapidly and easily performed in an integrated manner. Since the device has a syringe form, it may be prepared using a conventional syringe without need for a separate driving device and it is convenient to handle. Further, the device may fully remove bubbles and wastes from the specimen to prevent clogging in microchannels.

Figure 2:
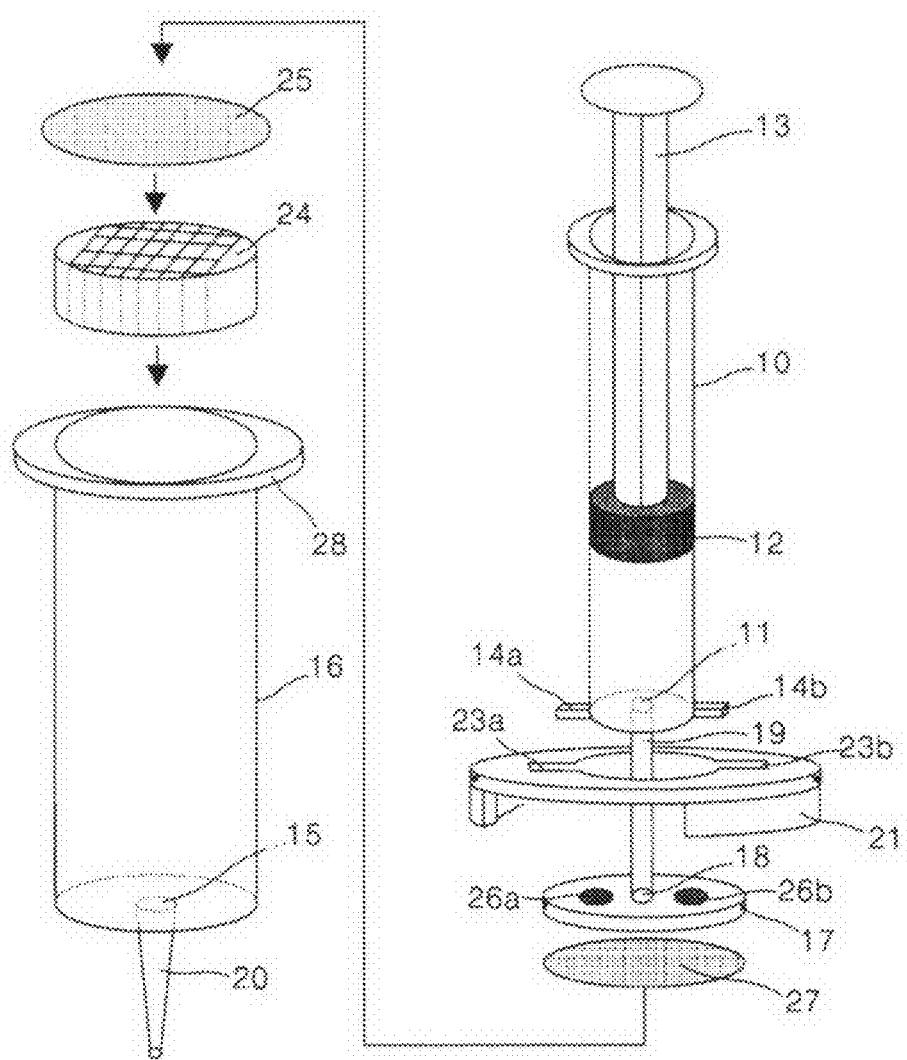
FIG. 2 is a schematic exploded perspective view of a device for pre-treating and injecting a liquid specimen according to another embodiment of the present invention.

FIG. 2 is a schematic exploded perspective view of a device for pre-treating and injecting a liquid specimen according to another embodiment of the present invention.

Referring to FIG. 2, a second piston 17 of a second syringe of the device further comprises vent holes 26a and 26b for discharging a gas.

The second syringe may further comprise a gas permeable membrane 27 which is impermeable to liquid, the gas permeable membrane 27 being connected to a bottom surface of a second piston 17.

Using the vent holes 26a and 26b and the gas permeable membrane 27, the device has an advantage that an increase of an internal pressure in a second tube 16 which may occur when a mixture of the liquid specimen with a treatment solution is injected into an exterior device may be prevented.

The second tube 16 has a second hole 15 in its bottom and a first tube 10 has two protrusions 14a and 14b in its lower and outer wall. The second tube 16 has a joint connection portion 28 in its upper and outer wall. A joint portion 21 is attachable to and detachable from the joint connection portion 28 in a clip form.

Figure 3:
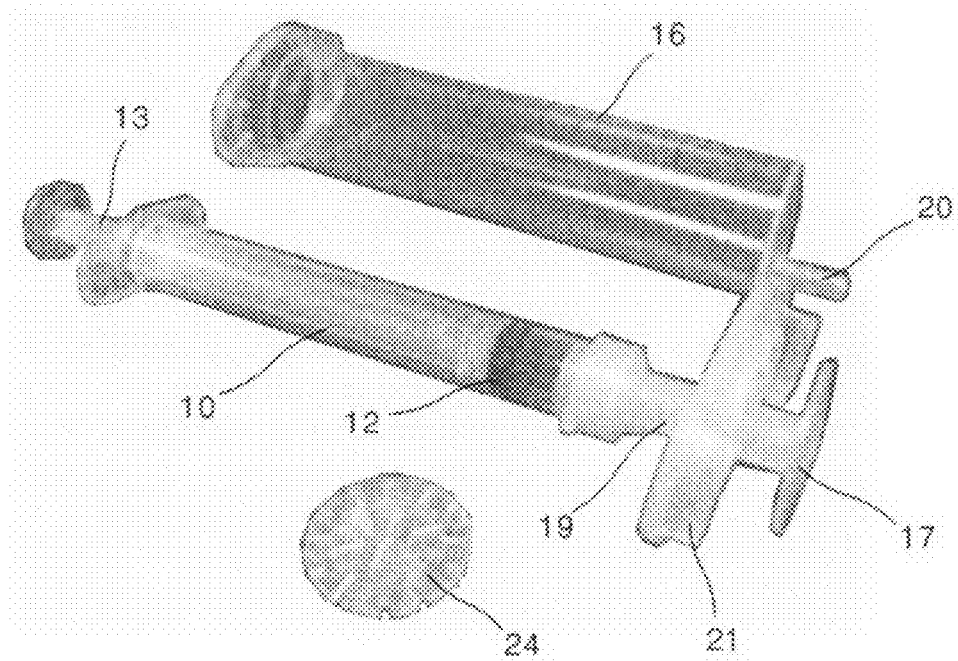
FIG. 3 is a photograph of the device for pre-treating and injecting a liquid specimen illustrated in FIG. 2.

FIG. 3 is a photograph of the device for pre-treating and injecting a liquid specimen illustrated in FIG. 2.

Referring to FIG. 3, the device comprises a second tube 16 having an outlet 20 in the bottom (see an upper portion of FIG. 3).

The device further comprises a first tube 10; a first piston 12 capable of moving along an inner wall of the first tube 10; and a first piston rod 13 connected to the first piston 12 in an upper direction of the first tube 10.

The device also comprises a second piston 17 capable of moving along an inner wall of the second tube 16; and a communication channel 19 fixing the second piston 17 to the first tube 10.

The device also comprises a filter membrane support 24 supporting a filter membrane (not shown) which is permeable to liquid but impermeable to gas, and having the form of nets.

The device further comprises a joint portion 21 being attachable to and detachable from a top of the second tube 16.

Figure 4A:
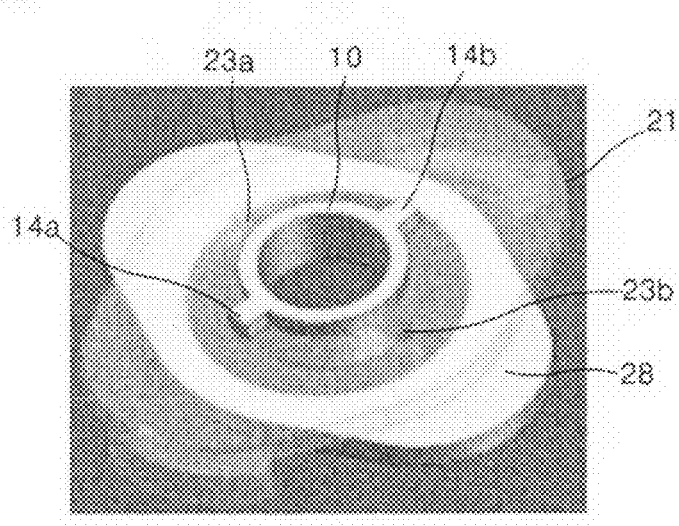
FIG. 4A illustrates a top 28 of a second tube, a joint portion 21 having grooves 23a and 23b, and a first tube 10 having protrusions 14a and 14b of a device for pre-treating and injecting a liquid specimen according to an embodiment of the present invention.

FIG. 4A illustrates a top 28 of a second tube, a joint portion 21 having grooves 23a and 23b, and a first tube 10 having protrusions 14a and 14b of a device for pre-treating and injecting a liquid specimen according to an embodiment of the present invention.

Referring to FIG. 4A, a lower portion of the first tube 10 is illustrated and the protrusions 14a and 14b are formed in a lower and outer wall of the first tube 10.

The joint portion 21 has an opening having a shape which corresponds to a transverse cross-section of the first tube 10 and the grooves 23a and 23b having a shape which corresponds to the shape of the protrusions 14a and 14b such that the first tube 10 can pass through the joint portion 21 when the protrusions 14a and 14b are matched with the grooves 23a and 23b. The protrusions 14a and 14b are not matched with the grooves 23a and 23b with an angle between the protrusions 14a and 14b and the grooves 23a and 23b being right angles.

The joint portion 21 is attachable to and detachable from the top 28 of the second tube, i.e., the joint connection portion. A method of connecting the joint portion 21 to the joint connection portion 28 is not specifically limited and may be easily selected by one skilled in the art. For example, the joint portion 21 may be connected to the joint connection portion 28 in a clip manner or screwed manner.

Figure 4B:
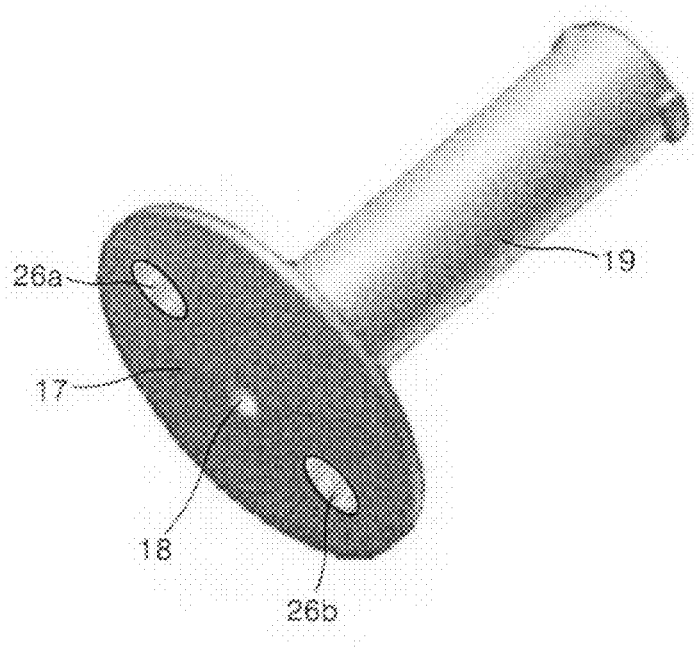
FIG. 4B illustrates a communication channel 19 and a second piston 17 of a device for pre-treating and injecting a liquid specimen according to an embodiment of the present invention.

FIG. 4B illustrates a communication channel 19 and a second piston 17 of a device for pre-treating and injecting a liquid specimen according to an embodiment of the present invention.

Referring to FIG. 4B, the second piston 17 has a third hole 18, and the third hole 18 is in a fluid communication with a first hole of a first tube (not shown) through the communication channel 19. Further, the communication channel 19 functions to fix the second piston 17 to the first tube. The second piston 17 further comprises vent holes 26a and 26b for discharging a gas.

Using the vent holes 26a and 26b and a gas permeable membrane of the device according to the present embodiment, an increase of an internal pressure in a second tube 16 which may occur when a mixture of the liquid specimen with a treatment solution is injected into an exterior device may be prevented.

The gas permeable membrane may be any membrane which is permeable to gas but impermeable to liquid. Examples of the gas permeable membrane include a cellulose ester membrane (available from Millipore).

Figure 5A:
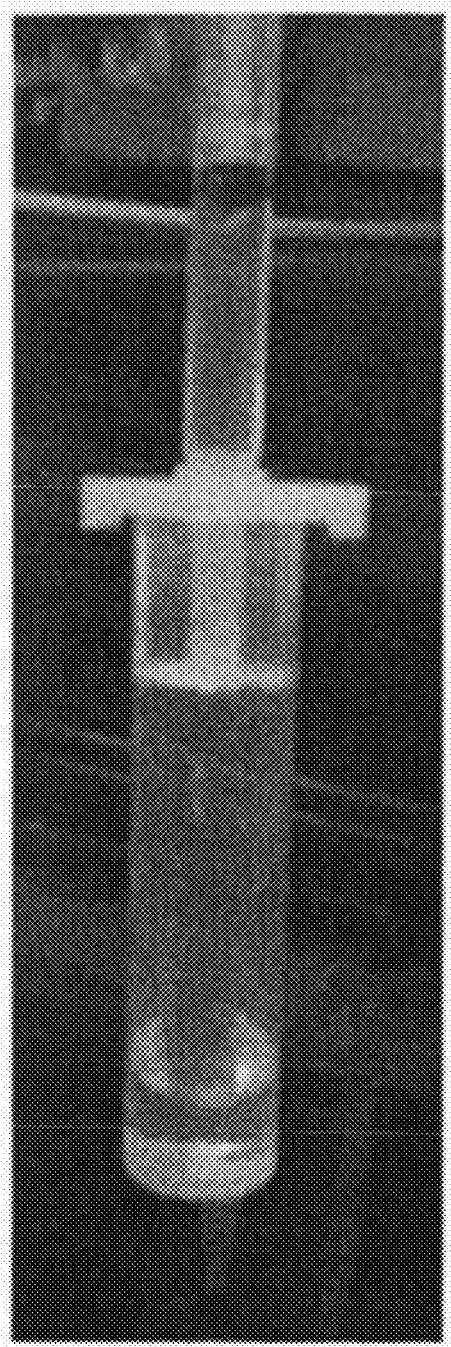
FIG. 5A is a photograph of a device for pre-treating and injecting a liquid specimen, which does not comprise vent holes and a gas permeable membrane, during operations.

FIG. 5A is a photograph of a device for pre-treating and injecting a liquid specimen, which does not comprise vent holes and a gas permeable membrane, during operations.

Figure 5B:
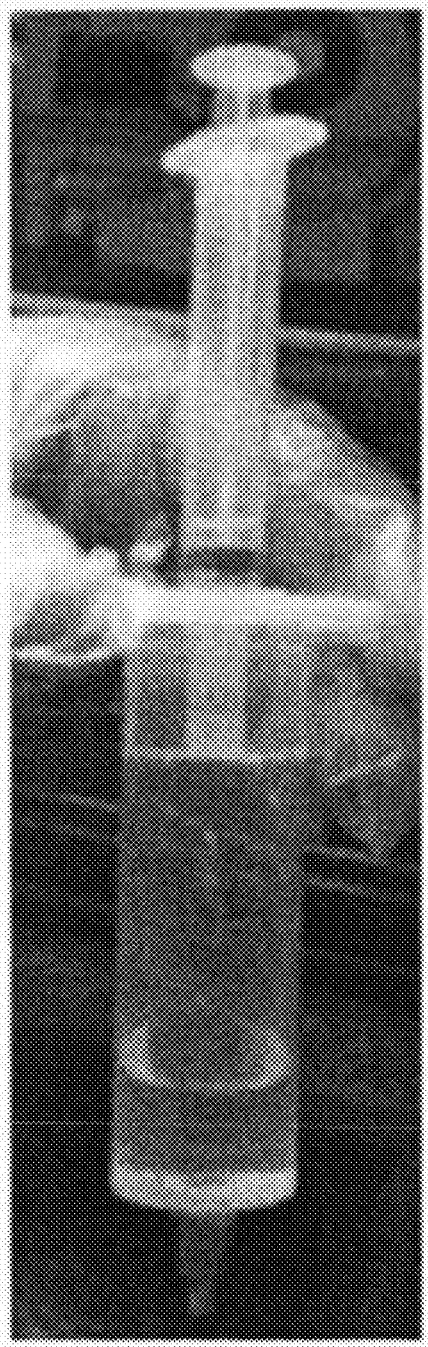
FIG. 5B is a photograph of a device for pre-treating and injecting a liquid specimen, which comprises vent holes and a gas permeable membrane, during operations.

FIG. 5B is a photograph of a device for pre-treating and injecting a liquid specimen, which comprises vent holes and a gas permeable membrane, during operations.

In another embodiment of the present invention, there is provided a method of pre-treating and injecting a liquid specimen, which permits collection, pre-treatment, and injection of the specimen in an integrated manner and can fully remove bubbles and wastes from the specimen to prevent clogging in microchannels.

FIGS. 6A through 6D schematically illustrate a method of pre-treating and injecting a liquid specimen using the device illustrated in FIG. 2.

First, in the method of pre-treating and injecting a liquid specimen, the liquid specimen is introduced into the second tube 16 of the device illustrated in FIG. 2.

The liquid specimen may be selected from the group consisting of saliva, urine, blood, serum, and a cell culture.

The introduction of the liquid specimen into the second tube 16 may be performed after the joint portion 21 and the second piston 17 are separated from the second tube 16. The introduction of the liquid specimen into the second tube 16 may be performed with a cap being connected to the outlet 20.

Next, a treatment solution is introduced into the first tube 10 of the device.

The introduction of the treatment solution into the first tube 10 may be performed after the second piston 17 and the joint portion 21 are again connected to the second tube 16 and the first piston 12 is removed from the first tube 10. The introduction of the treatment solution into the first tube 10 may be performed with the cap being connected to the outlet 20. The introduction of the treatment solution into the first tube 10 may be performed with the protrusions 14a and 14b of the first syringe being not matched with the grooves 23a and 23b of the joint portion 21.

Figure 6A:
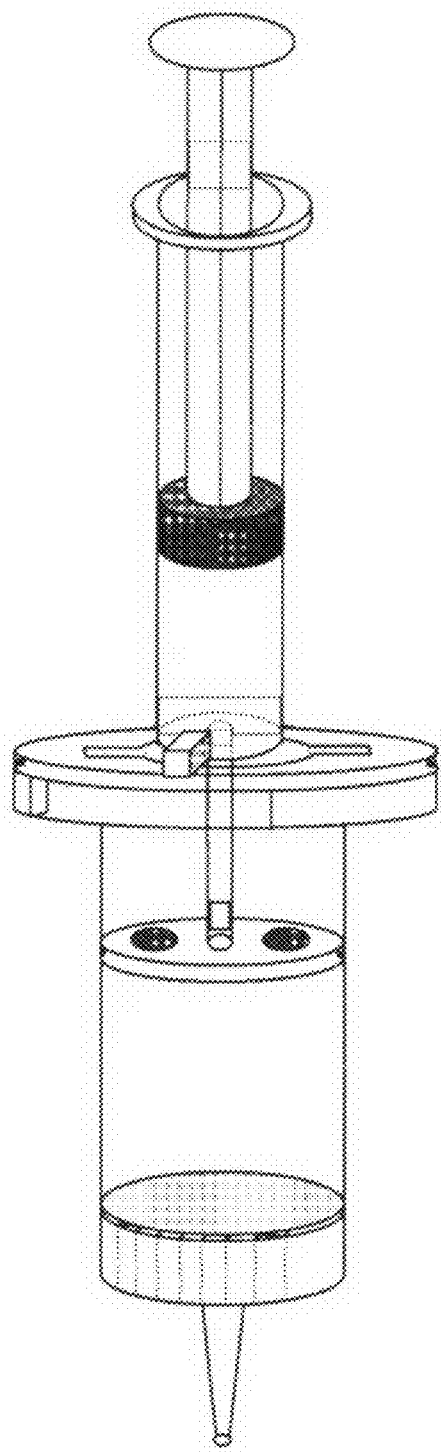
FIGS. 6A through 6D schematically illustrate a method of pre-treating and injecting a liquid specimen using the device illustrated in FIG. 2.

FIG. 6A illustrates the device after the liquid specimen is introduced into the second tube 16 and the treatment solution is introduced into the first tube 10. The liquid specimen and the treatment solution are not shown in FIG. 6A.

Next, the treatment solution in the first tube 10 is flowed into the second tube 16 through the communication channel 19 by moving the first piston 12 downwards without matching the protrusions 14a and 14b of the first syringe with the grooves 23a and 23b of the joint portion 21. The flowing of the treatment solution into the second tube 16 may be performed with the cap being connected to the outlet 20.

Figure 6B:
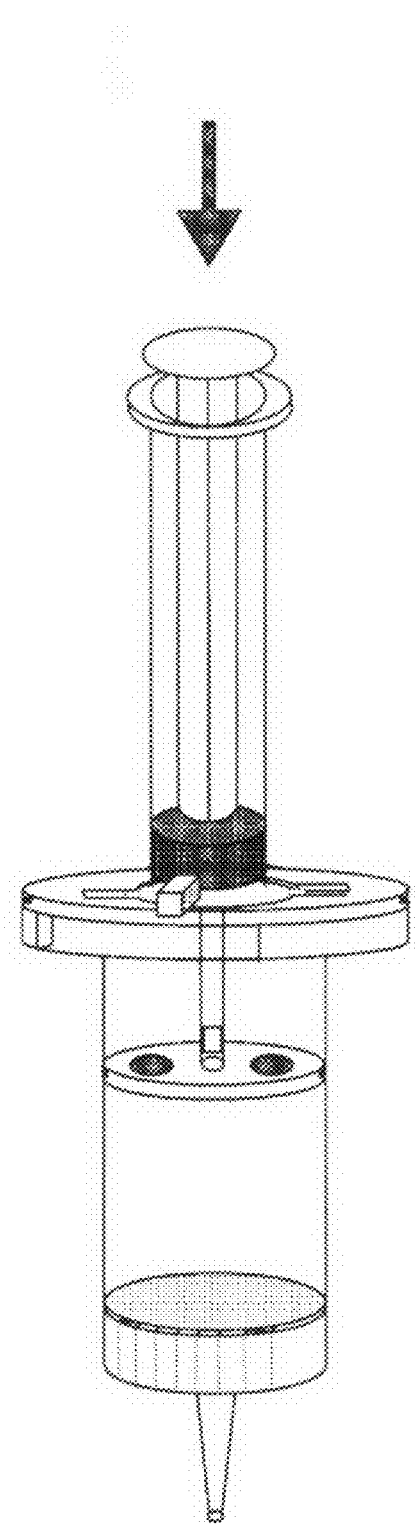

FIG. 6B illustrates the device after the treatment solution is flowed into the second tube 16. A mixture of the liquid specimen with the treatment solution is not shown in FIG. 6B.

Next, optionally, the liquid specimen may be mixed with the treatment solution. The mixing of the liquid specimen with the treatment solution may be performed with the cap being connected to the outlet 20.

Next, the first tube 10 is moved downwards with matching the protrusions 14a and 14b of the first syringe with the grooves 23a and 23b of the joint portion 21, to inject the mixed solution to an exterior device through the outlet 20 of the second tube 16. When the first tube 10 is moved downwards, the second piston 17 fixed to the first tube 10 through the communication channel 19 also moves downwards, and thus, the mixed solution flows out. The injection of the mixed solution to the exterior device may be performed with the cap being connected to the outlet 20.

Figure 6C:
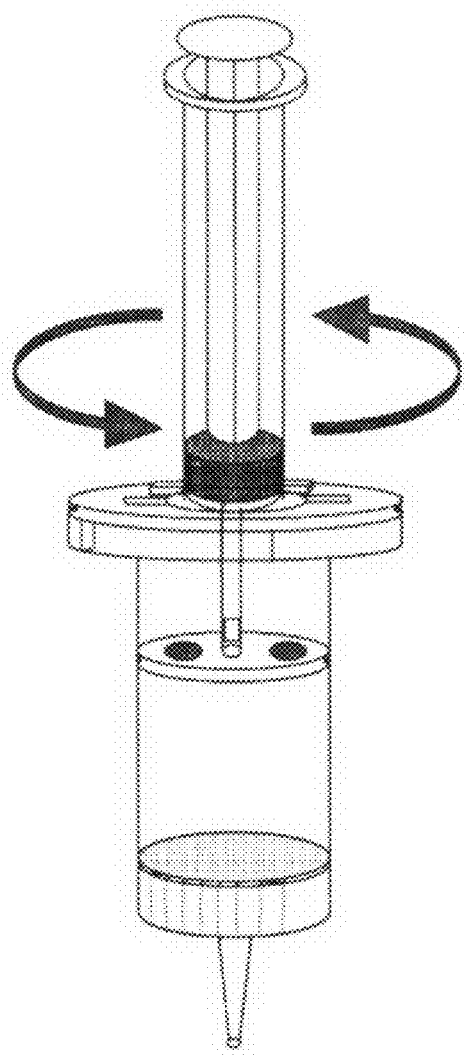
Figure 6D:
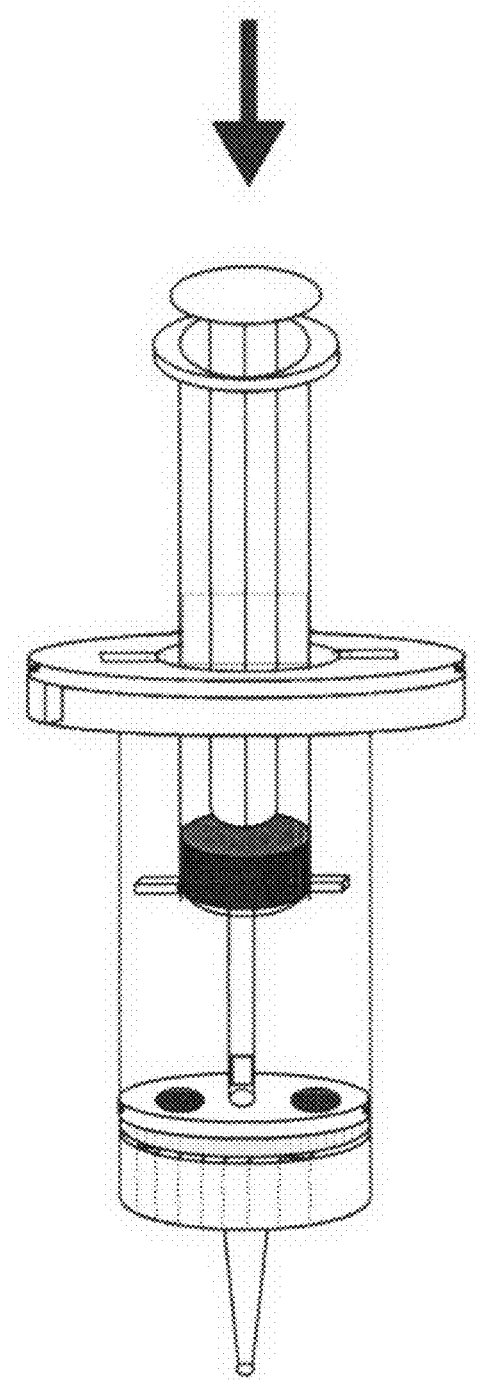

FIG. 6C illustrates the matching of the protrusions 14a and 14b with the grooves 23a and 23b. FIG. 6D illustrates the downward moving of the first tube 10 to flow the mixed solution to the exterior. The mixture of the liquid specimen with the treatment solution present in the second tube 16 and discharged to the exterior is not shown in FIGS. 6C and 6D.

The exterior device may be a microfluidic device, such as an LOC, for performing a series of biological analytic processes. Further, the exterior device may be a cell lysis device, for example.

Figure 7A:
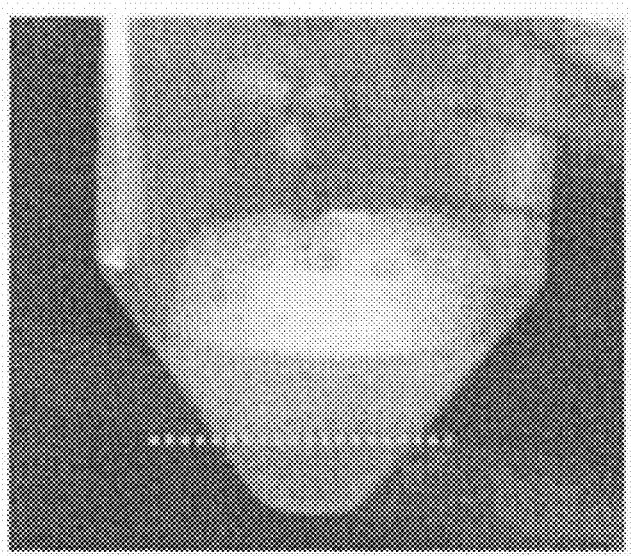
FIG. 7A is a photograph illustrating collected human saliva.
Figure 7B:
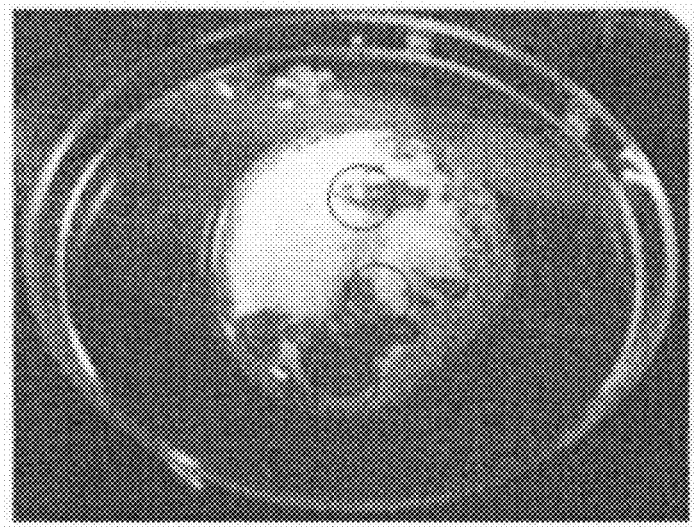
FIG. 7B is a photograph illustrating a solution obtained by mixing the collected human saliva with a buffer.

FIG. 7A is a photograph illustrating collected human saliva. FIG. 7B is a photograph illustrating a solution obtained by mixing the collected human saliva with a buffer.

Referring to FIGS. 7A and 7B, the solution obtained by mixing the liquid specimen, such as saliva, with the treatment solution, such as a buffer, contains much bubbles and food wastes (in the rings of FIG. 7B).

FIGS. 8A through 8E are photographs illustrating a method of pre-treating and injecting saliva using a device for pre-treating and injecting a liquid specimen according to an embodiment of the present invention.

Figure 8A:
FIGS. 8A through 8E are photographs illustrating a method of pre-treating and injecting saliva using the device according to an embodiment of the present invention.
Figure 8B:
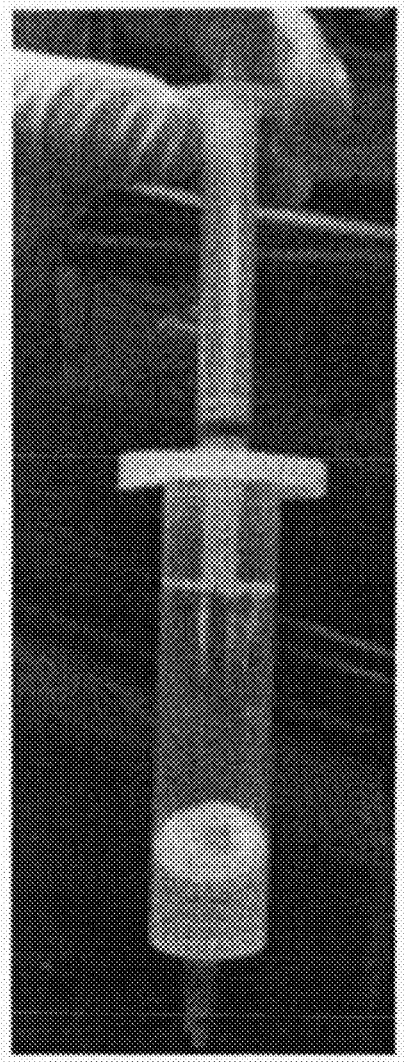
Figure 8C:
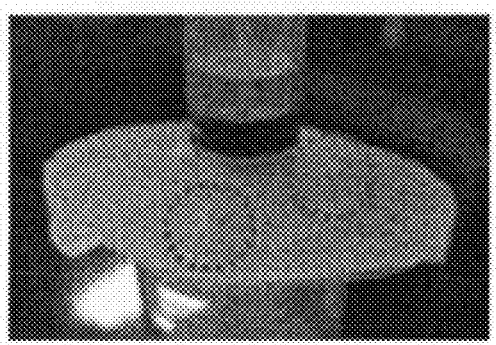
Figure 8D:
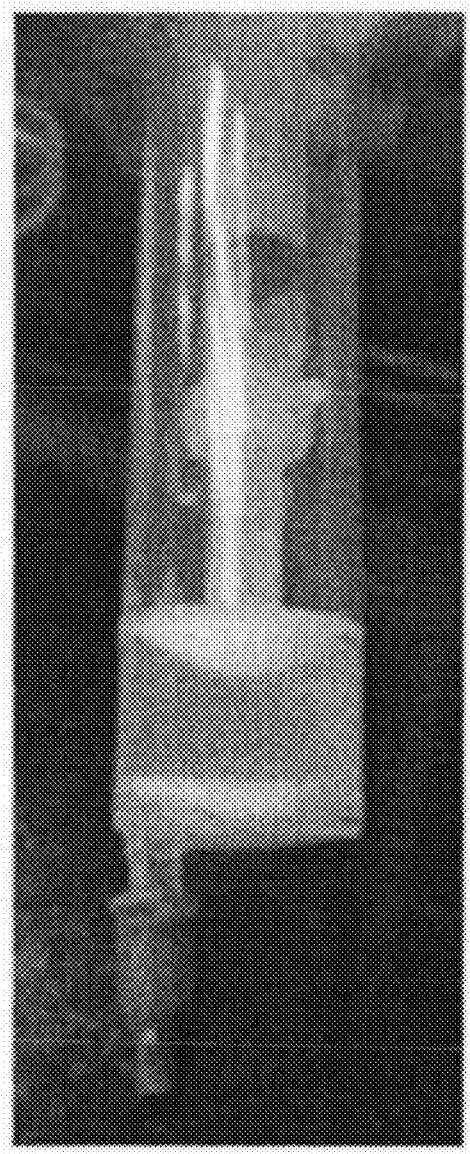

Referring to FIGS. 8A and 8B, first the saliva is introduced into a second tube (see FIG. 8A), a second piston and a joint portion are connected to the second tube and a treatment solution is introduced into a first tube (not shown), and then, the first piston is moved downwards to flow the treatment solution in the first tube into the second tube through a communication channel (see FIG. 8B). Next, the protrusions of the first syringe are matched with grooves of the joint portion (see FIG. 8C), and then, the first tube is moved downwards to flow the mixed solution to the exterior through an outlet of the second tube (see FIGS. 8D and 8E).

Figure 8E:
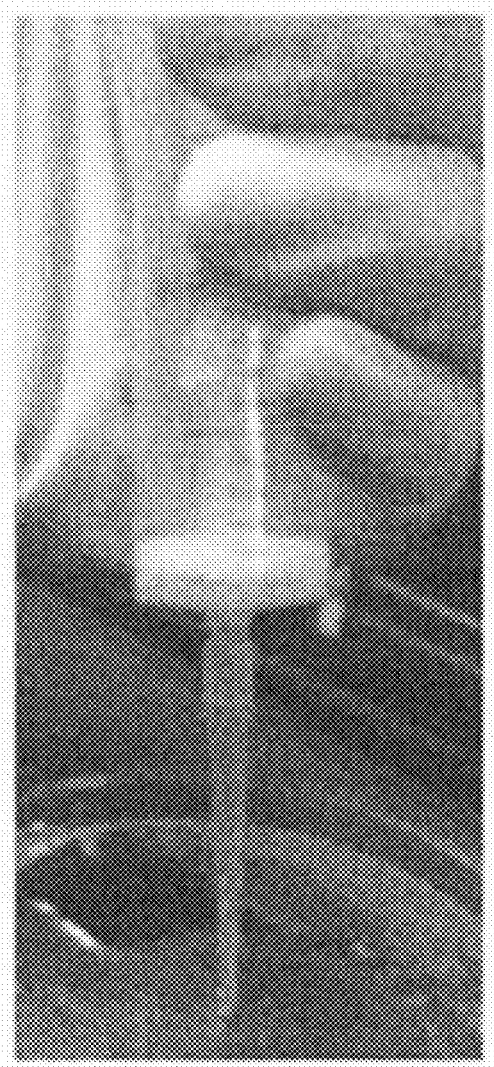

Referring to FIG. 8E, it can be confirmed that when the method of pre-treating and injecting a liquid specimen using the device according to an embodiment of the present invention is used, the liquid specimen injected to the exterior device does not contain any bubbles and wastes.

As described above, by using a device for pre-treating and injecting a liquid specimen according to the present invention, the collection, pre-treatment, and injection of the specimen may be rapidly and easily performed in an integrated manner. Since the device has a syringe form, it may be prepared using a conventional syringe without need for a separate driving device and it is convenient to handle. Further, the device may fully remove bubbles and wastes from the specimen to prevent clogging in microchannels. Further, the device comprises vent holes and a gas permeable membrane, and thus, an increase of an internal pressure in a second tube which may occur when a mixture of the liquid specimen with a treatment solution is injected into an exterior device may be prevented.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A device for pre-treating and injecting a liquid specimen, comprising:
    a second syringe comprising a second tube having an inner diameter, the second tube including an open top and a second hole in a bottom;
    a first syringe comprising:
        a first tube having an open top and a first hole in a bottom, the first tube having an outer diameter less than the inner diameter of the second tube;
        protrusions formed in a lower and outer wall of the first tube;
        a second piston capable of moving along an inner wall of the second tube and having a third hole; and
        a communication channel providing a fluid communication between the first hole of the first tube and the third hole of the second piston, and fixing the second piston to the first tube; and
    a joint portion being attachable to and detachable from a top of the second tube and having an opening having a shape which corresponds to a transverse cross-section of the first tube and grooves having a shape which corresponds to the shape of the protrusions such that the first tube can pass through the joint portion when the protrusions are matched with the grooves.

2. The device of claim 1, wherein the first syringe further comprises
    a first piston capable of moving along an inner wall of the first tube; and
    a first piston rod connected to the first piston in an upper direction of the first tube.

3. The device of claim 1, wherein the second syringe further comprises an outlet connected to the second hole of the second tube.

4. The device of claim 1, wherein the second syringe further comprises a cap being attachable to and detachable from the outlet.

5. The device of claim 1, wherein the second piston further comprises vent holes for discharging a gas.

6. The device of claim 5, wherein the second syringe further comprises a gas permeable membrane which is impermeable to liquid, the gas permeable membrane being connected to a bottom surface of the second piston.

7. The device of claim 1, wherein the second tube further comprises a filter membrane which is permeable to liquid but impermeable to gas, in its inner and lower portion.

8. The device of claim 7, wherein the second tube further comprises a filter membrane support supporting the filter membrane and having the form of nets.

9. A method of pre-treating and injecting a liquid specimen, comprising:
    introducing the liquid specimen into a second tube of the device according to claim 2;
    introducing a treatment solution into a first tube of the device;
    flowing the treatment solution in the first tube into the second tube through a communication channel by moving the first piston downwards without matching protrusions of the first syringe with grooves of a joint portion; and moving the first tube downwards with matching the protrusions of the first syringe with the grooves of the joint portion, to inject the mixed solution to an exterior device through an outlet of the second tube.

10. The method of claim 9, further comprising mixing the liquid specimen with the treatment solution, after introducing the treatment solution.

11. The method of claim 9, wherein a cap is connected to the outlet before the liquid specimen is introduced into the second tube and the cap is separated from the outlet before the mixed solution is injected to the exterior device.

12. The method of claim 9, wherein the liquid specimen is selected from the group consisting of saliva, urine, blood, serum, and a cell culture.

13. The method of claim 9, wherein the exterior device is a microfluidic device for performing a series of biological analytic processes.

14. The method of claim 9, wherein the exterior device is a cell lysis device.

15. A method of pre-treating and injecting a liquid specimen, comprising:
  introducing the liquid specimen into a second tube of the device according to claim 3;
  introducing a treatment solution into a first tube of the device;
    flowing the treatment solution in the first tube into the second tube through a communication channel by moving the first piston downwards without matching protrusions of the first syringe with grooves of a joint portion; and
    moving the first tube downwards with matching the protrusions of the first syringe with the grooves of the joint portion, to inject the mixed solution to an exterior device through the outlet of the second tube.

16. A method of pre-treating and injecting a liquid specimen, comprising:
  introducing the liquid specimen into a second tube of the device according to claim 4;
  introducing a treatment solution into a first tube of the device;
  flowing the treatment solution in the first tube into the second tube through a communication channel by moving the first piston downwards without matching protrusions of the first syringe with grooves of a joint portion; and
  moving the first tube downwards with matching the protrusions of the first syringe with the grooves of the joint portion, to inject the mixed solution to an exterior device through an outlet of the second tube.

17. A method of pre-treating and injecting a liquid specimen, comprising:
  introducing the liquid specimen into a second tube of the device according to claim 5;
  introducing a treatment solution into a first tube of the device;
  flowing the treatment solution in the first tube into the second tube through a communication channel by moving the first piston downwards without matching protrusions of the first syringe with grooves of a joint portion; and
  moving the first tube downwards with matching the protrusions of the first syringe with the grooves of the joint portion, to inject the mixed solution to an exterior device through an outlet of the second tube.

18. A method of pre-treating and injecting a liquid specimen,
  introducing the liquid specimen into a second tube of the device according to claim 6;
  introducing a treatment solution into a first tube of the device;
  flowing the treatment solution in the first tube into the second tube through a communication channel by moving the first piston downwards without matching protrusions of the first syringe with grooves of a joint portion; and
  moving the first tube downwards with matching the protrusions of the first syringe with the grooves of the joint portion, to inject the mixed solution to an exterior device through an outlet of the second tube.

19. A method of pre-treating and injecting a liquid specimen, comprising:
  introducing the liquid specimen into a second tube of the device according to claim 7;
  introducing a treatment solution into a first tube of the device;
  flowing the treatment solution in the first tube into the second tube through a communication channel by moving the first piston downwards without matching protrusions of the first syringe with grooves of a joint portion; and
  moving the first tube downwards with matching the protrusions of the first syringe with the grooves of the joint portion, to inject the mixed solution to an exterior device through an outlet of the second tube.

20. A method of pre-treating and injecting a liquid specimen, comprising:
  introducing the liquid specimen into a second tube of the device according to claim 8;
  introducing a treatment solution into a first tube of the device;
  flowing the treatment solution in the first tube into the second tube through a communication channel by moving the first piston downwards without matching protrusions of the first syringe with grooves of a joint portion; and
  moving the first tube downwards with matching the protrusions of the first syringe with the grooves of the joint portion, to inject the mixed solution to an exterior device through an outlet of the second tube.

* * * * *